United States Patent
Shin et al.

(10) Patent No.: US 7,427,481 B2
(45) Date of Patent: Sep. 23, 2008

(54) METHOD FOR IDENTIFYING A TESTICULAR CELL OF A CHICKEN

(75) Inventors: Ji Hye Shin, Gunpo (KR); Beom Ku Han, Seoul (KR); Heebal Kim, Seoul (KR); Jae Yong Han, Seoul (KR)

(73) Assignee: Avicore Biotechnology Institute Inc., Seoul (KR)

( * ) Notice: Subject to any disclaimer, the term of this patent is extended or adjusted under 35 U.S.C. 154(b) by 0 days.

(21) Appl. No.: 11/212,222

(22) Filed: Aug. 26, 2005

(65) Prior Publication Data

US 2006/0051797 A1 Mar. 9, 2006

Related U.S. Application Data

(60) Provisional application No. 60/604,696, filed on Aug. 27, 2004.

(51) Int. Cl.
*C12Q 1/68* (2006.01)
*C07H 21/04* (2006.01)

(52) U.S. Cl. .......................................... 435/6; 536/23.1
(58) Field of Classification Search ........................ None
See application file for complete search history.

(56) References Cited

U.S. PATENT DOCUMENTS 6,555,670 B1 4/2003 Aizawa et al. ............. 536/23.5

OTHER PUBLICATIONS

GenBank Accession No. CR387574, GI: 46240333, publicly available on Apr. 5, 2004.*
UniGene entry Gga.14561, UGID: 1248517, printed on Aug. 15, 2007.*
Kim et al. ChickGCE: A novel germ cell eST database for studying the early developmental stage in chickens. Genomics, vol. 88, pp. 252-257, 2006.*
Han et al. Gene expression profiling of chicken primordial germ cell ESTs. BMC Genomics, vol. 7, p. 220, Aug. 2006, pp. 1/6-6/6.*
Raymond et al., "*Dmrt1*, A gene related to worm and fly sexual regulators, is required for mammalian testis differentiation," Genes and Development 14:2587-2595, 2000.

* cited by examiner

*Primary Examiner*—Celine Qian
*Assistant Examiner*—Jennifer Dunston
(74) *Attorney, Agent, or Firm*—Clark & Elbing LLP

(57) ABSTRACT

The present invention relates to a nucleotide sequence of a testis-specific gene in avian species and a method for identifying a testicular cell of avian species.

1 Claim, 2 Drawing Sheets

SEQUENCE LISTING

```
<160> NUMBER OF SEQ ID NOS: 25

<210> SEQ ID NO 1
<211> LENGTH: 766
<212> TYPE: DNA
<213> ORGANISM: Gallus gallus

<400> SEQUENCE: 1
gcacgagggc gggctgcgcg ctgctctctc cgctcgcccc cgcgccctcc cgacccgccg      60
ggccagttcc gccgcccgct gcctccgcca gacatgacac aagactacga caataaaaga     120
cccgtgttgg ttcttcagaa tgactctctc tactcccaga gacgtcctta caccagcgaa     180
gatgaggcct ggaaatcctt tcttgaaaac ccacttacag cagccaccaa agctatgatg     240
agcatcaatg gcgatgagga cagcgcagcc gccctcggac tgctgtacga ttactacaag     300
gttccaaggg agaggagatc ttcaacagct aaaccggagg ttgaacaccc cgaccaagat     360
catagcaaaa ggaacagcat cccaaacgtg acagagcagt cacttatttc cactggagaa     420
aacagagtcc aggttctgaa aaatgtacct ttcaatattg tcctcccaca tacgccccag     480
atgggcatgg acaagagagg ccaccttaca accccgaca cgacggtcac cgtttcgatt     540
gcaacgatgc ccacccattc catcaaaacg gagacgcagc cccacggctt tgcagtgggc     600
atccctccca gcgtctacca ccccgagccc ccgagcggg tgggtggtgt tcgacaggaa     660
cctcactcct gaccagttca attccaacac ccagccacag aactcccaga ggcgaacgcc     720
ggactctacc ttttcagaga cccttcaagg aaggcgtgca agaagg                    766

<210> SEQ ID NO 2
<211> LENGTH: 722
<212> TYPE: DNA
<213> ORGANISM: Gallus gallus

<400> SEQUENCE: 2
gacttgagga ctgcgactcg agttgaggca tgcagaggaa ggctgggaga gagcctggag      60
gactccctgg gtagctgcag gttgtgcaga ggtttgggat cgttttttca aaagcttttc     120
aggtgaatta gggctacttt gagtcctctc tggaacactt gcaagtcctt ctccatgttg     180
tgccgcatgc tgtgaagacc caggccctct ttgcatgaaa gcctcaagcc ttggaaggca     240
gttgttggca ggtgagttgc ctctggcatt ctcatatagc acacgctctc ggtcagcttt     300
ttgctcaggg atggctgttc tgtcagcata tgggagttcc ccaaaacagc tgtgtcttac     360
agaacagatc ggactgttgt tcaacccttg tatgtggcag agcatccgtg ggtggggac     420
```

```
gttcctagtg agtatgttta cccatgagct gctggagcga aacaatgcc gacaggtatt      480 cattgtgtaa gctttcttat tctcttgcag agtgtcttat tgcagtgtct tattgcagag      540
caggttggct cttatgctct ccaaatgagg ctaaatgctg agaagcagag ctgcagaggc      600
ctccttgcca ggattccagg ttggcagttc cttccgtcga gttacaccag gttaacttcc      660
tcagtgggca gcaaccttcc ttgggtaggg gtttgcagcc gaggaggctg cagccctcgt      720
gc                                                                    722

<210> SEQ ID NO 3
<211> LENGTH: 776
<212> TYPE: DNA
<213> ORGANISM: Gallus gallus

<400> SEQUENCE: 3
gcacgaggtt ttttacaagt tccccttgcc aagctccact ccaaattttc aactatgatg       60
gcagtgtggc ttcaaagttt gagaaatatt taaaccaatt tcctaatgaa aattttcgct      120
gcctgaaatc tagcagctca tgcttatata gttattttt cagtcatcaa catgtatttt       180
attgctcagt gaataagaac caaacatgct ctctgttgtc agagttataa gtggaaagtt      240
tattccttct gtcacaattt tcctagcttt cttggagaac caattaatgt aaatacattt      300
tagtagtagc aggttttaat tgtttcagaa ccttcctggc agtatgggat gatttaatat      360
ttcatgtggt ttcctttcct gcttttgtac ttcaaagagt ggtgaacaaa ttagcaagaa      420
cttcagagcc agctactgtc ctgtagctgc acaactccca ccagctccag ctcgcaatcc      480
cttcttaatg gcttgaaatg gatacgtcct tatgggccca aatctgtgtc tgatgactga      540
actcttctga tggcagtgag aactaagcat gtggtaaagc tgcaggatca aacccttagg      600
aagcacatta cgctacagta cagcttaagg cagcttgtcc gccttggctt ctttagctat      660
aattgaacta atgtatttta atctgtacct catcttcttt gacttaatgt gaggaattaa      720
atttaaaata gctcattaag tacagtaatt tattcataca tcgaataagc tatata         776

<210> SEQ ID NO 4
<211> LENGTH: 706
<212> TYPE: DNA
<213> ORGANISM: Gallus gallus

<400> SEQUENCE: 4
gcacgaggct tggaccaagg cccttccccc gcttgctgac acaagctggc gggcagctgc       60
acttattccc agctgccatg aggcagccac agcaagttga atacaatata tacatgaaag      120
tcattaggtg cgcattggta gaactcaaag aaaagatgat aggttagttt ctaaatttcc      180
tgggttcctt agaaagtatt atgtgaaagt aaaacagctt tctctgcttg attatttttt      240
ggaattggaa ctgtctgcaa aaatattgca gttaaaactt tatacaggaa atgtagaaaa      300
attctgtcat tagccctata aacagtcag tctctagtga aatgcaaact ctgcttggat      360 gaagtttttag agatcttttc tgaaaaatac atttttcatct cagaagtgcc tatagttcag      420
aagagaagga agaaagaacc tgtaagtctg cagggatcct gctctggcga gtagctgtgt      480
tgaacagagt aatggttata gttctggaag attttacagg caatatatac cttccaaaat      540
cttgaatgca ccatgcttca aagtgttctt ctcctccctt ctctgttttt ctcaaaaaac      600
aaagcacttt ggattccaca catggaaagt atgtaataat ttcagctta tggagacatc      660 tgtgtaacta catgattgca cgctgcagag gaacttgatg taagcc                    706
```

```
<210> SEQ ID NO 5
<211> LENGTH: 889
<212> TYPE: DNA
<213> ORGANISM: Gallus gallus

<400> SEQUENCE: 5
cagaaagcct ttggatgaga gaactgcaga aatatatggg attaaatgct gcttctcgtc    60
tccattgtct gcaaggggca agtgtaggga tggtgtcatc ttcagccccc accggtgatg   120
taaactcttc tggtatgttg aactcttctg aggaagatgt gcctggttca tggggttgta   180
tggctgtgac gtatcccgcc cattgcttgc tgctatcgct gtctctatca acatcatttc   240
aattaagatc tccctgggaa ctgagggcag gatgggctg acgcagagct gctgggtgtt    300
gggatccatc tccgtgccgt gaggtggctg gaccctgtta cggggttgcct gggcaggtgg   360 tgatgcccgg tacccatcgt gctcaagaag catttgggca gtgccctcag tggcgtgttg   420
tgacctgggg tgagccctga ggtggtcagg cagctgggag caacggtctg agaaggtccc   480
atccagctga aaggaagcac gcgggctcct accggctctg ggacgcggc tcagcccggc    540 ctagccgagg cagcacagac ctcgtgtctg cggtgtcagt tgttctcag ctcctcaccg    600 ctgcctgcac cgatgtgggt gctgggagca ggctctgcag gcagcagtcc ctgccaaccg   660
cagccattca gctctctggc cgcgttcgag cccgatgaat ccaacttcc agcggctctg    720 cgcggcgagc ggtcctgggc tgccgctgag catccccggg ccgcgctcac ggggtggggt   780
tgcaccgccc ctgcagctcc ggccgcaaaa cgcggcgcgt atccgccctg ctcctcccga   840
gcagcgcgcg gtctgagaac tcccgagacg gcgactgaaa gcctcgtgc               889

<210> SEQ ID NO 6
<211> LENGTH: 420
<212> TYPE: DNA
<213> ORGANISM: Gallus gallus
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t

<400> SEQUENCE: 6
gcacgagggc cgcttcagca ccaggccggc cgcggacagc agcggccccg gctcggcggc    60
ggctctccgg tgcgggctgg gcggccgccg cggaaccata gccgtgccct gcgcgtccct   120
ctgcggcgtc ggatccctcg ccctttccct gcccgcttca tgttattact agtgacaaga   180
tgacaatcca tattttacc acatgatcca ttcagtcacc ccccacctc ccctgcccca    240 ccttctccac cctttgttct ttcttgtgat ttattttata taacattcca ctgatcatcc   300
actctcaccc cccctcctc ccctcccctc cgcgcccccc cccccgcccc gcccccggc    360 ccccgnaccc ccccccnccc ccccccccc cccnccccgc ccccccccc caccccccc    420

<210> SEQ ID NO 7
<211> LENGTH: 978
<212> TYPE: DNA
<213> ORGANISM: Gallus gallus
<220> FEATURE:
<221> NAME/KEY: misc_feature
```

```
<222> LOCATION: (23)..(23)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 7
gtttatttat ttattcattt atntgagatg gtattagnaa gcttttctcc actctttaga      60
aacaaatccc ttcagacaaa ggagaagaag caccaggcac atgtaggcaa tttctggtgc     120
ctcagacctc gcaagagggg ctcctcaggg cctccttcca ggctttgcat ggcccacgct     180
ggaattaagc ctttataagt tttctttcaa caaacctaca gcggggctta ctcatgcagt     240
ttgctgtttc tgaatgaagt cacgcatacc acgttcatgt ttgtgttaaa atactggaaa     300
gcgtttccct tttccttata ggaaaactgc atacatgacc tgcagtacag ctatttccaa     360
cgctcggctc ctcgggaaga ggagctgtgc caactctgcc cagcagcaca gagcacagcc     420
tccttgattt cagcgcatcc gagatcctct cctcgggat caggtgtcca taactccacg      480
gctgcagttc attctcttga gcctccgata cctgcaaaag ctgcttttat gtttccttag     540
gacaaaatga aggcgggatc caaaaaaaag actccgaggt caaaaaaaaa cactcactgc     600
catatgtttg tgctgttggc atcaccgcag tgatccaggt gctcgtgtgc tgagaacctc     660
tgcactgcct gcgctgacat cctggattgc tgcagagaca caggtacagg tgggatcagt     720
gacaccagtg ctgcagtctg tgtgcagtga ggcacagctc ccagccctgc tggcactgct     780
caccgctcgc caatagcaca ggaggtgatc tgaaaactga aacgtttag ggctactaaa      840
cctcaccctg tgaccctgtg tgttgtgaac gacctcactg gtttcttttt actcacgtcc     900
tagcggaggc atgggatctg tttccctcag tactgttttg tttcagtttt tttcccttaa     960
atggccacag cctcgtgc                                                    978

<210> SEQ ID NO 8
<211> LENGTH: 783
<212> TYPE: DNA
<213> ORGANISM: Gallus gallus

<400> SEQUENCE: 8
gcacgaggcc tcgtgccgcg cctgcgcaga agctatagga cagcctccct cacctcctcg      60
gcggctttct gttccctgag ggaagggaat ggggtggttt tcctcttggt ctacgaggat     120
tcaaacgtgc ggatgcccct ctttatctgt tctgcatcat tctgtggcga agtcacattc     180
tgccatttaa acaaaaccag aagtacagca atgtgctctc tgacgtttag ccaaaacctg     240
agggacagag atctgcccca gctgatccct ggcaactaat tcagagtctt cagcaaactg     300
aggttctgcc tagagaaagt tgttttttcct ggatagtggg acatctgaag cctcacagca     360
gagtcttggt gttccacaag ctgtgaggag gtgcactgta cctgctaggg ctgagaacag     420
gttgaggaga tgataaaaaa ctaagaagat tttttgtaaa tcttttttt tttttttaa       480
ccaaatatga gccctgacct acccagcaca cgactaaagc tttgcttta gcaacaacga      540
gcaggaaagt gccaagtgca gtcatcccga ttcttcctaa atactatagg gaaggtcaga     600
aactaattga aacgtaaagg ttctgggaaa ctgatggaag tgtcacctct cagttcagca     660
agacccacat cattacctct ttcagaaata aatattttc tcacatgcac attacaaagt     720
tgatttaccc tgagcggcca tacacaacag taagcttatt cccattatta ctttttggca     780
tcc                                                                    783
```

<210> SEQ ID NO 9
<211> LENGTH: 710
<212> TYPE: DNA
<213> ORGANISM: Gallus gallus

<400> SEQUENCE: 9

| | | | | | |
|---|---|---|---|---|---|
| gcacgaggcg | gcaaccggcg | cggaggtggc | cgtactcgtg | tgcgcgctgt | tcataggaga | 60 |
| accaatgact | gtgtgctata | tttgggaagg | tgctgatgaa | ttttagtacc | attcagattc | 120 |
| cagttgtgtc | ccaacatgga | tgtggttgaa | tcagcctcca | cagaaatctt | caagaaaata | 180 |
| cccagtgttc | tgggcagcct | ggtggaggaa | cctaaaaaga | gacatgctat | ccccaatcac | 240 |
| ctgctggaat | caaaggttta | ttcagaacgt | aagaagagca | atgttataca | ggcagagcct | 300 |
| gctgtattac | actatggagg | gtatgaagtt | ggaaaacatc | accagcagac | actgaagctg | 360 |
| ataaatattt | ctgacaatgt | aataaaccct | cacattatac | caccccagac | aaagtatttt | 420 |
| ctgatcaaat | acaacaaaac | acatcgactt | gtccctggct | tgtcatatgt | ggttactgtt | 480 |
| gattttgtc | ctgatgagtg | gcgttattac | tatgactgca | tccgaattca | ctgtcaggga | 540 |
| gaagatacat | tagttgttcc | tgtgcatgct | taccctactg | tgaatgtgtt | ggaatttcca | 600 |
| tcatttataa | atatgtctga | tgtatccatt | ggtcagagta | aggagtatgt | tatcccgttg | 660 |
| cagtgcagtt | gcccgataga | ctttgaattc | cacattgatt | ttattcagcc | | 710 |

<210> SEQ ID NO 10
<211> LENGTH: 749
<212> TYPE: DNA
<213> ORGANISM: Gallus gallus

<400> SEQUENCE: 10

| | | | | | |
|---|---|---|---|---|---|
| gcacgaggtg | agtttgttat | ggcaacaggg | ctgttatgaa | gccagccaag | aacaggacct | 60 |
| cctgtgatca | tagtgtcctt | tgaaccagga | cagctagttt | caagttttct | atatggaaat | 120 |
| cttgtgaaaa | gaagaacatc | cctggaggca | ctttgatgtc | aacaggtgtc | tctcacattc | 180 |
| agaaaggatc | tctgctgaag | accaggaaat | gcaagatgat | ttgaaagaac | ccagcaatct | 240 |
| agaggaatta | agacattcat | tccaaagagc | tatggacaaa | ctagtgaaag | atattgagct | 300 |
| tacattacag | gaaacccaga | ataatgataa | caagaggcac | aggaagcagc | aacaagtaaa | 360 |
| gatgcaggga | gcctcgagtg | acataccaac | atcatatttc | atctcagaca | atacaactga | 420 |
| gaacatggat | gctaggagtc | atacagcaca | cttggatggg | atgggaagaa | ccagtgtttt | 480 |
| gcagcctgaa | gtatccacca | atgtggaaga | gcagaaagag | atctgctgca | tgcaggtcac | 540 |
| agctgctgac | attgaacttc | agaggatgtg | gtgtaatttt | gtgctggctg | aacagaaata | 600 |
| tgaatatgaa | gagataatgg | cgcagattca | tcatcaggta | gttaaaagag | cagtaagtag | 660 |
| gaaaaagaga | aagagttgag | cccagtagag | attgaaacat | tcaattcctg | tgttaagaac | 720 |
| ttgtgtaagt | ttaaaaaaaa | aaaaaaaaa | | | | 749 |

<210> SEQ ID NO 11
<211> LENGTH: 959
<212> TYPE: DNA
<213> ORGANISM: Gallus gallus

<400> SEQUENCE: 11

| | | | | | |
|---|---|---|---|---|---|
| tttaacaagc | aggataaacc | aagcgttgcc | tctgtataag | ctgtgctgtc | cattcaggcc | 60 |
| tgagcacgct | tgctctgtgc | tcgtggtttc | ttgcaggacc | ggtgacgaa | tgaccactgg | 120 |
| gagtatgtgc | tgccacacgg | ttgcaatgtg | gagaaaaagc | tgagctgggc | tgtgggagct | 180 |

```
gcggctgtca gcgtgtggtt ccataagcag gctgcatccc tgtgtggtcc ccgtgaccgt    240
gcagaggagg ctgtgctgct tgcaggttct gggaggctct gttgctttgg ctcttaaata    300
aaagcagtgg tccctggcag gaaggagcac ggggaaggtt ttccctgtcc tacactcgtt    360
ctgaggattg gagtaaatgc attggcagag aagcagagaa gtttcttgtg gtccctcttc    420
cgggctgcca gaccccagct ggaacagctg ctgtcgggt ggcatagctc tgcagggatt    480
atgactgggc acacaggatg gtgaacgttt attcgtgggt ttggtccagc aagggagttc    540
tgctgatgtc actttcttaa acagagccta ggatggccct aaagcaaacg gtgcccgttg    600
aggctggagc acaccgctga cgtttcggtt tcaagctccc tgtgtgcccc acggaggtgc    660
cacctgcatt tccccagcct aattgccaag cttgcatggg ctgcgcttgc agcccgctgg    720
gattcatctg tggatgcgca gagccctggc cttgaggaga tgctgctggc agggaaggga    780
ctccctcctg cggacgggaa ggccgcagag acgcgaaaac ggagcgggct gagtccggct    840
tgcagatacc ttcccgcgag cgcgtggtta cgtctggtag cgcccacggg ccgctcagac    900
tgctggcggg cgcgagtaga acgccgcgct gccgcacaac gcggagccgc gcctcgtgc    959

<210> SEQ ID NO 12
<211> LENGTH: 296
<212> TYPE: DNA
<213> ORGANISM: Gallus gallus

<400> SEQUENCE: 12
gcacgagggg cgggctcccg gccccggcag gcagcgctcc tccctcccgc cccgggagcc    60
cccggcgggg tgacagccca gccgagccca gccagccgc cctgcccggc ctcggcccgc   120
tcgccgccag cgaggcgaca gccgcctccc cgcgcccgcc atgtggaagc tcaacaagag   180
cagcaaagtt ctcctggacg actcccccga ggaggaggag acgcggcccc gcggcccgct   240
gccgtccgcc gccgccttcg cggccccca cactaaacac cagcttcttc atgacg       296

<210> SEQ ID NO 13
<211> LENGTH: 815
<212> TYPE: DNA
<213> ORGANISM: Gallus gallus

<400> SEQUENCE: 13
gcacgagggt agaacttaag aagagaaaaa agattcctac agctagggca tgggaaaaag    60
acagaaaaac agaaactctt taatttgcta gcactttgca aattatttga agctccagag   120
actcatatat gccagtattt tcataagctc acttgtttct tccagcatgc catttgaaga   180
gtgccaagtg aatgaagcta ctgagctgtg tttacttatt tcctcagtgg tgacaaggct   240
aacaaacatc ttgagcacaa attctgttga gatgaggtgt gattccccat caatacagct   300
atgctggcag aaatctgtcc tagtccaaat gaggtctttg atagtcatta aaacctgaat   360
tttacacata atcacatgta actttaactc ggcttgttaa tgtggttttt gccttcctgc   420
ctgattcttt cttcactacc ttgcaatttc agagtcattt atcttttttcc agctggctgc   480 agactcctac taaagctgaa ctgagttaga aaatgattga tttgatgttc tgggggtgag   540
gaccaagcaa gcagaatcta ctgatatcac tcactgtggt agtcacatac agaattttaa   600
ttctcattac aagacacagc tttgcctgaa cagctgcacc ttttctagaa ctttatcatg   660
actaaggaga ttttatttgt ataggtatat gagactcgta ctagcaaaac acagcacaat   720
catttccaaa catagcatga gaaactgcaa aaaggagagt cctgatgcta aaagtatagc    780
```
agactgaggc ttacattacc ttgccagcac acctg                          815

<210> SEQ ID NO 14
<211> LENGTH: 523
<212> TYPE: DNA
<213> ORGANISM: Gallus gallus

<400> SEQUENCE: 14
gcacgaggga agaaaccaca gtgcaagaaa agatgggaaa tccagtgatt ctttaatcca    60
taccaaacac tactatgaaa agagaacagg tagctgttac tacaacagcc ataagccaag   120
gcaatgctac ataagcttta aacacctgaa gtctaatagg tgaagtcatg tactcacatt   180
aacagtgtgt ttgagaacat gaccgacaaa gcaactaggt cagcaactga ttaatcccag   240
gcacgtttgt agtctaatct gtgctttaaa ataacaacag aaaacccaag ccctgctagc   300
aaaggcctac agaagacagt aatgattaga ggacatgcag accaggaaga gccatccaaa   360
tacaagatat taagcatttt aaattgtaag ttgatggcac gtggcttctg aatggtagtt   420
accaaataaa tgaaagtaac tagacatttt taaagtgtct gataaaaaca gaagagtaag   480
tctttaaaaa aaaaaaaaaa aaaaaaaaaa aaaaaaaaaa aaa                     523

<210> SEQ ID NO 15
<211> LENGTH: 729
<212> TYPE: DNA
<213> ORGANISM: Gallus gallus

<400> SEQUENCE: 15
cacgagggtc ctccagccct cctcacctca gctccctctt ccaactgtgt cattgcatct    60
acacatacag ataaacaaca gccccttcac tttctagagt ccctgactaa tcttcttcct   120
catgccatgg catcttctta cccaacacca agcacaaggc aatgctattc tatccctcac   180
cctgtcctca gtcttgttgg tcaccatttt ctttcctgag tgctaataag ggagatgggt   240
tttctaggaa catccctgtg ctttctggga gtgtagaagg gaaccaggac cactggttca   300
gcaccttgcc cagttgtgga gcattcacat aggtgcagaa aagctttgca gctgctggaa   360
gtcatacatt gaaacttaac tgagcaagga tcaccaagca ttggaaaacc tcagctgaaa   420
gattctaccc agcagcaagt ttttagtatc aaagtaatat aaattgaaa ttgttctaaa    480 acaaatacca ggttaattta ctgatgatga cagtaataag cattaaatat tttattatta   540
agtgaaaagc aatgaccttg attcgacgcc cactagagta atcttcgat tgaattattt    600 tactgttgaa taattaacag tgaccctgat ttgctgaaca tgcaggtaac agaagctgtc   660
agttaactag attctgagga ctgagcgtgt gccttgtgct gggctagatg gtacatcctg   720
ggagcttcc                                                           729

<210> SEQ ID NO 16
<211> LENGTH: 704
<212> TYPE: DNA
<213> ORGANISM: Gallus gallus

<400> SEQUENCE: 16
gcacgaggct gaggaggtgt ccagcaaggc tgtaccatac agatcacccc cagccccct    60 cccaaataaa taaataaaaa caagtaagaa ttattttca ttacagctgc cataatacac    120
tggtccatgt gatgaaacct gcaatggcaa gattcaactg ctgtggttca ttctctgctg   180
ttttccttcc ctgcaaattt tccttgtgaa aggcacagaa acaagatgcg tattctgcaa   240
taacggacaa agaggagcta gaaaggaaa gggacagaac agaaagtttg acttcagcac   300

```
ccaaatcctc ataagaaaag ttacgctcta actaaaagga taaggaaata cagttagtgt    360
ctggataact tacttcactt ttaatgtttc tgcaaattcc aacatgaaca ggcccaatgt    420
aaatcagctt tcctcactga gctgacggct aaactacagc agatgccaga ggattttaa    480 actgcacagg tcacatttag aggctgatgc agtacaatgc tgatattgtc tactagcttg    540
atttcagcat tcccttttgaa ggtagaaaag cactttgcaa aagactgaga gaaaacagtt    600
cttcacttgt gccctcagaa tatgttttta aactacctttt tcatttctaa tgtaaagaca    660
aagaaaacta gtcactagag aatcactatt aaatataata taac                     704
```

<210> SEQ ID NO 17  
<211> LENGTH: 635  
<212> TYPE: DNA  
<213> ORGANISM: Gallus gallus

<400> SEQUENCE: 17

```
gcacgaggga ggccttctca ggcattacag gatccccttc catggctttg cagtcatcct     60
catgcaagtt tgagcttctc ccagactctt ttgactcttt ttgtgttgtc ctctgaagca    120
gcgtcttcct cttttggact atcaatctct ttcactctct ggctcatttc ttctatggtt    180
ctgggcaccc cttttgttg tgtaggcctt tccaataaca gggtaaacct gtcagtggga     240
agtgtgcagg actgtatgta taggacagag agtacagagg tttcctggtt ctcattctgg    300
cacatcccct acccaagcct tgtggatga acacatccgt cacttcacaa aggaagttct     360
tgagttgctc ctagaagctc attccctcaa caacaaaatg tccccatctg ccctcgctg     420 ggctccccag gccccgcttc ttgtcccaga gcaacaactg cagtgactct catggcttca    480
gtgacacact gcaaaagctc caagaccaaa acagtagaa tctgttgagc acacaaactt     540 tcttttacagt caggcatctg cagtagagca gagggggggag tttctctctt atctcacgca   600
agacatcaga atttgcttac aaagcatgca ttcct                                635
```

<210> SEQ ID NO 18  
<211> LENGTH: 806  
<212> TYPE: DNA  
<213> ORGANISM: Gallus gallus

<400> SEQUENCE: 18

```
atggtgatgg tgaggaaagg tcatgttttt gatacgtagg caaaaaaaaa ttattcctga     60
ttctgattaa atttcagggt gtacatgcca ctgccaatgg ctgcaatcaa aagcatttgc    120
tctctttctc agaagaaagg gaaaaaaaaa gcagcaattt actatcgtaa ttataagatg    180
aaaactcagc tttacagacc taaaacatga aaatcctgca gaacaatttt aatatcaaat    240
ttttcagagc ttcgttaagt tttacccaac cacagtcagc tgtccagaag acagcttact    300
gtgactgtgt ttaaatgctg tcctttgcat cctgctctgt gcaaccatgt gtgctgaagg    360
tggccatggg actgcactcc ccagcagtca cgctggcagg cgtaattagt gtctactcca    420
tcatcagtgc tttaaaaagt gtgttttata aggttagtca tcactctgcc actccactac    480
tgatctcaac agccgtatat aaaatcctct tccccagcag gccctgccag gctgcatacg    540
gtgctttcaa aggaacaaca ccaatgataa cagcaagcct gggaacagcg tgtctaggtg    600
ctgttaggaa ctggttcccg ttaattaatg gataaggttg tatcaggtca tgacactgga    660
tggtgtggga tcaggtggat ttgtggcttc tctcgacagt gtagttttct cctgtgttgt    720
gtggccataa gcaacagggc ctgctgcaaa gggggaaaga gatataggta aaatcaaata    780
```

```
aatataaatc tgaaagtgcc tcgtgc                                              806

<210> SEQ ID NO 19
<211> LENGTH: 704
<212> TYPE: DNA
<213> ORGANISM: Gallus gallus

<400> SEQUENCE: 19
gcacgaggct cagccatctc aggccagtat atctataatt ttgtccctaa gttttttgatt        60 aagaagaaag ctaagatcca aaatagtcca gttcctctaa agtgttttaa gacttctctt       120
ttccaaggtt ttcagctatt tctgtaatga tctgaattca gaagagttcg actgaatcag       180
gcagtgtcga ttcagtgtcg actgaatctt acgctccagc ctgaagcaaa atttgatggc       240
tagaaattcc aaatttctgt attttttcta tttacgtgca tagtgattat gctgtaagtc       300
agaggtgttt tttcaggaag gtgccaggct tggagcaatg ttatttaaag tcatcactct       360
tctgaaaata atcagtattt gataatgtgg tgctactgtg cacagttaat gtgttaccat       420
gaaaaacgag caaaatgtac tggtttggga gctagccctt gggttctaga ctatcagagg       480
tagctggagg tgaaggagat ggagaggacc ttctaccaaa atgtaccatt aaaaatttcc       540
tgcggttcct gcttctgtga tgttgagctc tctctgagcg cttgctttcg taatgaaaac       600
taaatagaga tgtttcttat ggaattctta aatagagcca gcattactac cccggttgtt       660
taactgtaaa tcacaatagc ctggagagtc tcagtggtgg ggaa                        704

<210> SEQ ID NO 20
<211> LENGTH: 664
<212> TYPE: DNA
<213> ORGANISM: Gallus gallus

<400> SEQUENCE: 20
gcacgagggc cgcagggcag gcccatcatg caggaagcca ttttacacct tcagttgtca        60
cctgcatctg caggagttgg tgtttcacac acctgctgag acatgaggcc tcctaactgg       120
tggcactgga ggagaaatac tgtagcagct tttatttctg gtgaaataca gccaggtaac       180
tgggtgtgaa agcagaaggg cagacaaaag tggattggtg gtgagagaaa tctgtttgag       240
cattttcctg gaattgtctt ttccctctca tgctgtttgc agtgtttccc ttctgttact       300
ttagcctctg gataaaaata gagagagcct tataaaagag aagataaatc ctttccatag       360
tggattgtag gtcattgata tcgcctggct ccaaaagcaa gctgcaatct ccagctgaag       420
aaaacttatg cattgagaaa atccaattcc ccttggtctg ctgtgaaggc ttcaataccg       480
ggttcatcca gaaatatgca tcttgtagaa tactgaaaga tgtctctgag ctaagttact       540
gatatgccac agcaattcat ctacttgaag aaatatggat ttgtcagcaa aggtttcctc       600
tgtgctggga gtgggtcaga gccagcaggc actgcgttgg gcgctgaggc aacatgcagc       660
cggg                                                                    664

<210> SEQ ID NO 21
<211> LENGTH: 755
<212> TYPE: DNA
<213> ORGANISM: Gallus gallus

<400> SEQUENCE: 21
gcacgaggca cagcaggttc ttgtgtttct gtacatgttg taaggaatta accaccaacg        60
ggaaatttaa attaccatac attttcttaa ctcttgtggt ctcactctga gatgcatttt       120
tgagatgaga gcaagcttgc atttaaaaaa aaaaaaaaaa aaaaaaaaaa aaaagcttgt       180
```

```
tggaatgcag taatactgat gctgggttta ttcaacaaat ttttaatgtt aatatgtaaa      240
acataactct gcctaaagtg gtaatatcag aaaggtatgt gatcaaacat catgaacaaa      300
taataattgt atgcactatg tgacaggttc tctgttgtta agaatacaag tttggctcta      360
ttaataatga cttagtgtaa aaaaaaagtt atttggaaat ttactacagt cttcatagat      420
gataaagagg tagtacagta ataagatatg actctggaca gggtgaaagg aaacagggtc      480
ctacatgtat tctctgtgct agctgtgaat gcaagtggct gatagaaaac ctcatatcag      540
atatagttta atatgtaatt catttttttgg agaggatgtg tgttgtaaac tccaaagaag      600
aaagagtgga taaacttcct ctgctttgtt cttctcttgg acattactaa gttggagcaa      660
tggacacaag gaatagatat tatttacaat taaataaaaa tggctctctt caaggtttgt      720
gaatccagac ctcatctgca gctcctcaaa tattt                                 755

<210> SEQ ID NO 22
<211> LENGTH: 696
<212> TYPE: DNA
<213> ORGANISM: Gallus gallus

<400> SEQUENCE: 22
caggctcagc aggctcacac gcaggcttgc tccagccgtt ctgatgggct gttttcctct       60
cccctcctct gttcttgcct cttcctcct ttcagctggc ctctcactca cttgtgcttc      120
agagaaaaac tcattttccc cagagagcat ctccacatct gttaatagct tatctttcct      180
tgaaataact gcatagctgt tctggcaggc ttctctgctg ttttctttct gttttgctgg      240
aaaggatgag ggggctccctt caggttcttc atcccagaca aggtctgtgc tggtttcccc      300
agtttcctca ttgcaggaga gagcaatatt actctgcttg atataatctc gtattctctt      360
cttatggaag gcttccttag aagttgtgta ctcctcttcc agccttttca cgttttcctc      420
tgtgagagca gagctggaat ctgatggaac agtcccaggc gaaatatttt ttggtgggga      480
ctggttactg ccagaccctg acagcttgca tccattagac atatctgcaa tgcattaagg      540
agatgaggct cttcagcaac aggcaaagtc aattcatcat tctttctggg caggagtatc      600
caggagagca ggaaaggaga ccaccctacc caaggccaac aagggcaggc agagacctgg      660
tggtggtgag atgaccagga caccctcccc tcgtgc                                696

<210> SEQ ID NO 23
<211> LENGTH: 551
<212> TYPE: DNA
<213> ORGANISM: Gallus gallus

<400> SEQUENCE: 23
gcacgaggac acgatgtcgg aggcggcggg ttgtgccttc ccctcaccgc cgggcgctgc       60
cgtagccacg cagcgggcag cacggagggc ccggggccgc cccgcgggaa agctgtgggt      120
gcgaatcgcg gcagagctgt ggagcagccg tggctctcag ttccgaatta acggctgcaa      180
acgctgcacg tgctcccctc gctggttttct catttatgcc gttttctttt aaccgcggca      240
gaagcacagg aggaacacgc agaatcactc cctcacagca tgtttgtgta accaccacca      300
caacgggtag tttgcagcac atgcgaactc ctccactccc aagtgagta aattcaccga      360 aacaacacag aggctgtgca gaagctgcta acagttacct tcttcagccc cgctgttgaa      420
gtgctgaaat cttctgtagt tttaattca agcagattga acaaagctcc tggaatacag      480
aactcaatta tccgagaagc gggtttcaaa ccaacagtta agtcacagat cagcaaaggc      540
```
caacagaact c                                                          551

<210> SEQ ID NO 24
<211> LENGTH: 1090
<212> TYPE: DNA
<213> ORGANISM: Gallus gallus
<220> FEATURE:
<221> NAME/KEY: misc_feature
<222> LOCATION: (62)..(62)
<223> OTHER INFORMATION: n is a, c, g, or t

<400> SEQUENCE: 24
attgtgaggt tcagaagcat ttatttattt tgtttgaaca ttttgagagt acatgtctga     60
tntgctatat gggtcagcat ttaaggtgat tgcaagtaac ttcatgacac agctaaacat    120
aagcttgtgc tgtgtgttct gtgggactcc atttgtcata tgatacccttt taaatgttga   180 gttagtttgg taacttatca catccgttta gaagtacaac caaaaccagt gatattatct    240
cttgaacctg catctagtgc agcctttacc aattgttcac tgatgtagct tgctgcattg    300
tcatagagtg ccttggaagt gaccccacct tttcctgcaa tttgtgattc acaaccggac    360
aggtatgttt ttgtgtcctc ttcaaaatgt gtaggtggct acaatccac tggcagtgta     420 gtcttcagca gttgctggcc agtataacct acaggcttgt cacgtgatac cttaaaatct    480
gttttttcag ccagttgtgg atctgagtca taaatagata gatatgcttt tgtacaatgt    540
tgagtctgca ggtaacttgg actagttgca tggataatgt ctctttcttc tgattctgtg    600
gtttgtgaat gtggcagaga actgttacgt agataaactt ttctgtcctc tgactgtttc    660
agttcttcag agctgacttc tgtgctagaa tcacactgtt ttatccctct tttctttgga    720
cgtatctcat cattactgaa aagtatcggt tctggatcag cttgattgtt gtggtcatca    780
atttccttag gaacaactcc attttttactt tgcaagtagc tcgtcctaga acattttggc    840
tttccatgtg taaggctgct ttttgagtca gggagaaaaa tctctgtatt ggagtccagc    900
atctctgttc caacttgctg ataattcata gcctttgagt ctcttaactc ttcttcagaa    960 agggtatca aatactggca gttatacaga gaagccccgt tttgttgaat acattcatac    1020
gttctcagat aatgagtgaa tgtggttagt gttaatgcac atacttgctt gtaatccaaa   1080
accctcgtgc                                                          1090

<210> SEQ ID NO 25
<211> LENGTH: 773
<212> TYPE: DNA
<213> ORGANISM: Gallus gallus

<400> SEQUENCE: 25
gcacgaggct ttatctagtc caattttgaa tatttccaag aatggaaatt ccacagttgc     60
acagagcgac ctgttccagt ccttattcac gttacttcag tgggcaaaag gacaccataa    120
ttctttctaa gcatctttca gttttttgctt ttaggctgct gtgatattct tcaaaggagg    180
aaagatccaa gatgggcctg atggctagaa acagagtctg tatcctgaaa taaatagata    240
cacatttttc catgtatataaaa ttatttttcc ttatacctca gtcatttta tgatcattca    300 taccaccgca atcaaaatgc tagatcaaat attgttttta gcaagtaatt ttgtacccac    360
acacagataa attatatata tacatatgtt ttgtatgtgt atttgtaata tagcatacat    420
tcatacatga attaaaggtc attgttgtgg atcttccttt ctaagcatct gtgcattttc    480 tttttttctct cttgtaaata tatattctgt gtttgggtgc acatgctgca catgatttag    540
aacccattta ctcacatgcc ttcatctcgg agagcacctg aaatcactgg tgtaactgta    600

-continued

```
gtgcataact ttgggcacct tcataacttt ctgctggtct gagtgtgtat tggaagcgtc    660
agattcagat tacaccctct ggtagcgaac aaaatggaga aaaatctcct ccagaatggg    720
gtgatttgca gatagatttc atgattcatc cacaagggta cctcactgat cac           773
```

US 7,427,481 B2

METHOD FOR IDENTIFYING A TESTICULAR CELL OF A CHICKEN

CROSS-REFERENCES

The present application is a non-provisional patent application claiming the priority to U.S. provisional application Ser. No. 60/604,696 filed on Aug. 27, 2004. The entire contents of this application are incorporated herein by reference.

BACKGROUND OF THE INVENTION

1. Field of the Invention

The present invention relates to a nucleotide sequence of a testis-specific gene in avian species and a method for identifying a testicular cell of avian species.

2. Description of the Related Art

Expressed sequence tags (ESTs) are short segments of deoxyribonucleic acid (DNA) that are generated from either one or both ends of expressed gene transcripts (Adams M. D., et al., (1991) Complementary DNA sequencing: expressed sequence tags and human genome project. *Science* 252, 1651-6). Most of the ESTs were produced for genome-wide analysis using microarray technology and deposited in the dbEST (Boguski M. S., et al., (1993) dbEST—database for "expressed sequence tags". *Nature Genetics* 4, 332-3) of the National Center for Biotechnology Information (NCBI). Currently, the dbEST is the most abundant source of new coding sequences. Up to Jul. 23, 2004, 22,830,690 ESTs from 721 species were deposited in the dbEST. In the species having relatively higher number of ESTs compared with its protein sequences, the EST data are probably more important resources for extracting biological and evolutionary information of the species.

Especially, the number of EST sequences in the chicken (*Gallus gallus*), which is currently reported 495,089, is more than 60-folds than that of protein sequences. Based on plenty of the chicken EST data, the institute for genomic research (TIGR) have produced *Gallus gallus* gene index (GGGI). The TIGR gene indices consisted of clusters of EST sequences and the clustered elements were evaluated to produce a set of unique and virtual transcripts with high fidelity, called Tentative Consensus (TC) sequences (Quackenbush J., et al., (2000) The TIGR gene indices: reconstruction and representation of expressed gene sequences. *Nucleic Acids Research* 28, 141-5). To date, TIGR has assembled the chicken ESTs with chicken transcripts into 43,866 TC sequences.

The testis is the organ that produces sperm, and during spermatogenesis transcriptional regulation within germ cells is carefully orchestrated (P. Sassone-Corsi, Unique chromatin remodeling and transcriptional regulation in spermatogenesis. *Science* 296 (2002) 2176-2178). Sperms develop in association with highly specialized somatic testicular cells, such as Sertoli cells and Leydig cells. During the differentiation of germ cells into spermatozoa, a complex paracrine dialogue with Sertoli cells occurs (M. K. Skinner, et al., Cell-cell interactions and the regulation of testis function, *Ann. N.Y. Acad. Sci.* 637 (1991) 354-363). Endocrine activity such as testosterone secretion by Leydig cells promotes germ cell differentiation (M. D. Griswold, The central role of Sertoli cells in spermatogenesis, *Semin. Cell Dev. Biol.* 9 (1998) 411-416). Thus, it has been speculated that the testis has specialized transcription complexes that coordinate the differentiation program of spermatogenesis. In birds, the female is the heterogametic (ZW) sex, but genes on the W chromosome do not influence gonadal development in the way that the SRY gene on the mammalian Y chromosome does. No sex-chromosome-specific SOX gene homologous to the mammalian sex-determining gene SRY has been found in birds (R. Griffiths, The isolation of conserved DNA sequences related to the human sex-determining region Y gene from the lesser black-backed gull (*Larus fuscus*), *Proc. R. Soc. Lond. B. Biol. Sci.* 244 (1991) 123-8). However, SRY-like HMG-box gene 9 (SOX9) may influence gonadal development by the initiation of transcription of anti-Müllerian hormone (AMH) during the early stages of chick gonad differentiation (E. Oréal, et al., Early expression of AMH in chicken embryonic gonads precedes testicular SOX9 expression, *Dev. Dyn.* (1998) 522-32). The avian DMRT1 gene is located on the Z chromosome (I. Nanda, et al., 300 million years of conserved synteny between chicken Z and human chromosome 9, *Nat. Genet.* 21 (1999) 258-259) and is expressed more strongly in male than in female embryonic gonads, (C. S. Raymond, et al., Expression of Dmrt1 in the Genital Ridge of Mouse and Chicken Embryos Suggests a Role in Vertebrate Sexual Development, *Dev. Biol.* 215 (1999) 208-220; C. A. Smith, et al., Conservation of a sex-determining gene, *Nature* 402 (1999) 601-2; Z. Shan, et al., Sex-specific expression of an evolutionarily conserved male regulatory gene, DMRT1, in birds. *Cytogenet. Cell. Genet.* 89 (2000) 252-7).

It is therefore thought that numerous genes affect male germ cell development in birds and, that some of these may be expressed in a testis-specific pattern. The chicken is one of the most important model organisms for the study of germ-line development, as its embryonic development occurs in ovo.

Throughout this application, various publications are referenced and citations are provided in parentheses. The disclosure of these publications in their entities are hereby incorporated by references into this application in order to more fully describe this invention and the state of the art to which this invention pertains.

SUMMARY OF THE INVENTION

Under such circumstances, the present inventors have made intensive researches to identify novel testis-specifically expressed nucleotide sequences involved in spermatogenesis in avian species, and as a result, discovered novel testis-specific nucleotide sequences in avian species.

Accordingly, it is an object of this invention to provide an isolated nucleotide sequence of a testis-specific gene in avian species.

It is another object of this invention to provide a method for identifying a testicular cell of avian species.

Other objects and advantages of the present invention will become apparent from the detailed description to follow and together with the appended claims and drawings.

DETAILED DESCRIPTION OF THIS INVENTION

Figure 1:
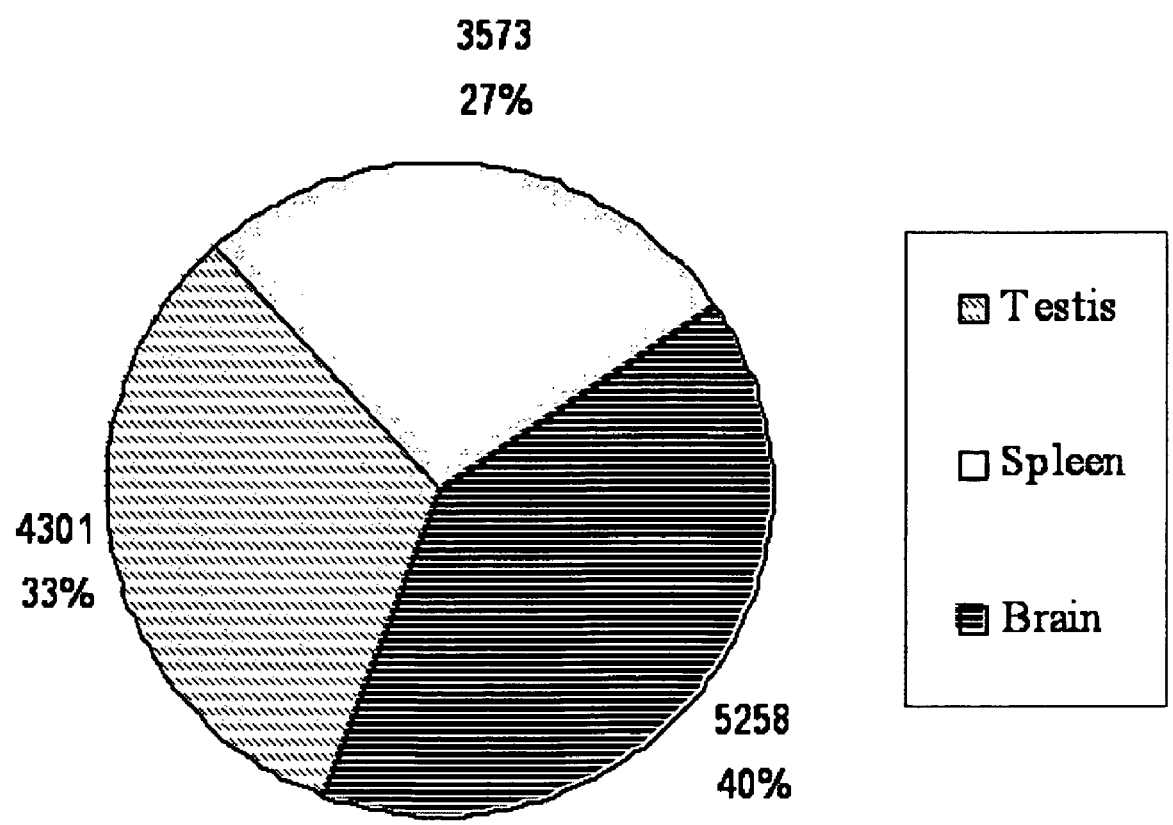
FIG. 1 represents the proportion of ESTs collected from the Korean native chicken (KNC). Brain, spleen, and testis tissues were dissected from 26-week-old KNC and cDNA libraries were constructed from total RNA isolated from each tissue. 17,502 cDNA clones from the libraries of each tissue were sequenced and successfully read 13,132 sequences.

In one aspect of this invention, there is provided an isolated nucleotide sequence of a testis-specific gene, wherein said nucleotide sequence is specifically expressed in a testis of avian species and comprises (i) a nucleotide sequence selected from the group consisting of SEQ ID Nos:1-25, (ii) its complement or (iii) its fragment.

The present inventors have identified testis-specifically expressed nucleotide sequences for elucidating mechanisms and processes underlying spermatogenesis in avian species. To demonstrate the expression specificity of nucleotide sequences in avian testis, the inventors have researched on various organs such as testis, brain and spleen and as a result, discovered novel testis-specific nucleotide sequences in avian species.

The testis-specific nucleotide sequences are differentially expressed in testis of avian species, preferably, a chicken, a quail, a turkey, a duck, a goose, a pheasant and a pigeon, more preferably, a chicken.

According to a preferred embodiment, the testis-specific nucleotide sequence consists of (i) a nucleotide sequence selected from the group consisting of SEQ ID Nos:1-25, (ii) its complement or (iii) its fragment.

The nucleotide sequences of the present invention comprise not only a nucleotide sequence selected from the group consisting of SEQ ID Nos:1-25 but also complementary sequences thereto. The complementary sequence includes a perfectly complementary sequence and substantially complementary sequence as well. The term "substantially complementary sequence" used herein means a nucleotide sequence hybridizable with a nucleotide sequence selected from the group consisting of SEQ ID Nos.1-25 under conventional stringent conditions. Details of "stringent conditions" are found in Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985). The stringent conditions may be determined according to temperature, ionic strength (buffer concentration) and the presence of other compounds such as organic solvents. As understood by those of skill in the art, the stringent conditions are sequence dependent and are different under different environmental parameters. For example, the stringent conditions are provided by (i) washing with 0.015 M sodium chloride/0.0015 M sodium citrate/0.1% sodium dodecyl sulfate at 50° C. or (ii) hybridizing at 55° C. by use of, as a hybridization buffer, a solution containing 50% formamide, 2×SSC, and 10% dextran sulfate followed by highly stringent washing with 0.1×SSC containing EDTA at 55° C.

In addition, the nucleotide sequences of this invention comprise fragments of a nucleotide sequence selected from the group consisting of SEQ ID Nos:1-25.

It may be appreciated that numerous genes affect male germ cell development in birds and that some of these may be expressed in a testis-specific pattern. Accordingly, the testis-specific nucleotide sequences found in this invention could support such consensus in the art.

The novel nucleotide sequences of this invention can be applied to the following uses owing to their testis-specific expression pattern: (i) identification of testicular cells; (ii) discrimination of sex; (iii) separation of sperm; (iv) treatment or induction of infertility; and (v) gene diagnosis (specifically, gene diagnosis of infertility). For example, for discrimination of sex, total RNA extracted from early embryo is subjected to Northern blotting (Peter B. Kaufma et al., *Molecular and Cellular Methods in Biology and Medicine*, 102-108, CRC press), or cDNA prepared total RNA is subjected to hybridization reaction. Where the nucleotide sequences of this invention are applied to treatment of infertility, they may be introduced into testicular cells from birds having infertility due to gene deletion. In contrast, the nucleotide sequences of this invention contained in testicular cells of birds are manipulated to inhibit their expression for induction of infertility. Furthermore, the nucleotide sequences of this invention may be used for gene diagnosis, in particular, genetic polymorphism analysis.

In another aspect of this invention, there is provided a method for identifying a testicular cell of avian species, which comprises the steps of: (a) hybridizing a DNA molecule obtained from a cell with the testis-specific nucleotide sequence described above; and (b) analyzing the occurrence of the hybridization of step (a), wherein the occurrence of the hybridization is indicative of the testicular cell.

The testicular cell identified in this invention refers to a cell population present in testis tissue including spermatogonial stem cell, any germ cell (spermatogonial cell, sperm and spermatozoa) derived from spermatogonial stem cell, Sertoli cell, Leydig cell and muscle cell associated with connective tissue, preferably, spermatogonial stem cell, spermatogonial cell and sperm, more preferably, sperm, and most preferably, sexually mature sperm.

According to the method of this invention, it is preferred that the preparation of a DNA from cell to be analyzed is performed by reverse-transcribing mRNA isolated from the cell to obtain cDNA. In a specific example, RT-PCR (reverse transcriptase-PCR) is carried out to prepare cDNA. The isolation of total RNA may be performed according to conventional processes known in the art (Sambrook, J. et al., *Molecular Cloning. A Laboratory Manual*, 3rd ed. Cold Spring Harbor Press (2001); Tesniere, C. et al., *Plant Mol. Biol. Rep.*, 9:242 (1991); Ausubel, F. M. et al., *Current Protocols in Molecular Biology*, John Willey & Sons (1987); and Chomczynski, P. et al., *Anal. Biochem.* 162:156 (1987)). For instance, total RNA can be readily extracted from cells using TRIZOL (extraction solution).

The DNA (e.g. cDNA) prepared thus is preferably labeled. For labeling, materials detectable by spectroscopic measurement, photochemical measurement, biochemical measurement, bioelectronic measurement, immunochemical measurement, electronic measurement, chemical measurement are used. For instance, the labels include, but not limited to, radioisotopes such as $P^{32}$ and $S^{35}$, chemilluminescent compounds, labeled binding proteins, heavy metal atoms, spectroscopic markers such as fluorescence markers and dyes, and magnetic labels. The dyes, for example, include, but not limited to, quinoline dye, triarylmethane dye, phthalein, azo dye and cyanine dye. The fluorescence makers include, but not limited to, fluorescein, phycoerythrin, rhodamine, lissamine, CY3 (cyanine fluorescent dye) and CY5 (cyanine fluorescent dye) (Pharmacia). Labeling is performed according to various methods known in the art, such as nick translation, random priming (Multiprime DNA labeling systems booklet, "Amersham" (1989)) and kination (Maxam & Gilbert, *Methods in Enzymology*, 65:499 (1986)).

According to the method of the present invention, the hybridization of a DNA obtained from a cell is carried out with referring to the procedures described in Southern, E. *J. Mol. Biol.* 98:503 (1975) in the hybridization conditions optimized through modifying several factors (salt concentration, temperature, reaction time and probe concentration) (Joseph Sambrook, et al., *Molecular Cloning*, A Laboratory Manual, Cold Spring Harbor Laboratory Press, Cold Spring Harbor, N.Y. (2001)). For example, the hybridizing reaction may be performed by hybridizing at 55° C. by use of, as a hybridization buffer, a solution containing 50% formamide, 2×SSC, and 10% dextran sulfate followed by highly stringent washing with 0.1×SSC containing EDTA at 55° C.

According to the method of the present invention, the occurrence of hybridization is analyzed with various methods known in the art, particularly, depending on the types of labels used. For example, fluorescence microscope, preferably, confocal fluorescence microscope is used for fluorescence labels, and the intensity of the signal detected with such instruments increases proportionally to the extent of hybridization.

The present method permits to exactly identify testicular cells of avian species, preferably, a chicken, a quail, a turkey, a duck, a goose, a pheasant and a pigeon, more preferably, a chicken.

The following specific examples are intended to be illustrative of the invention and should not be construed as limiting the scope of the invention as defined by appended claims.

EXAMPLE I

Preparation of Tissues

The Korean native chickens (KNC) used in this study were kindly provided from the National Livestock Research Institute (NLRI) in Korea. The KNC had been domesticated in Korea approximately 2,000 years ago and KNC successfully adapted to local environments and climates. Although the KNC is considered to have relatively low capacity of egg and meat production compared to commercialized broiler or layer strains, the merits of KNC were also reported; the resistance to epidemic avian disease and the thick egg shell (Han S. W., et al., (1995) Estimation of Heritabilities and Genetic Correlations on Major Economic Traits in Korean Native Chicken. *Korean Journal of Poultry Science* 22, 67-75; and Ha J. K., et al., (1997) Studies on Thickness of Eggshell and Eggshell Membrane of Korean Native Chicken. *Korean Journal of Poultry Science* 24, 29-37).

In this study, brain, spleen, and testis tissues were dissected from brown-colored KNC at 26 weeks.

EXAMPLE II

Construction of CDNA Libraries and Sequencing

Samples of chicken tissues were homogenized and total RNA was isolated using TRIZOL (extraction solution) reagent (Invitrogen, Carlsbad, Calif., USA) and poly(A) mRNA was purified using the PolyATract mRNA isolation system (Promega, Wis., USA) according to the manufacturer's protocol. The libraries were synthesized using the ZAP-cDNA synthesis method (Stratagene, Calif., USA). The cDNA was prepared, size-fractionated, and inserted into the Uni ZAP XR vector using an XhoI linker-primer and EcoRI adaptor. After in vivo excision with *E. coli* strain SOLR, the cDNA libraries from the testis contained inserts ranging from 0.5 to 3 kb (n=20). After white/blue selection, colonies were picked randomly from rectangular plates (23×23 cm) and transferred to 384-well plates using a Q-BOT (robot system) (Genetix, UK). The plasmids were purified using a Montage Plasmid Miniprep 96 kit (Millipore, Mass., USA). Sequencing reactions were performed by priming at the 5' end of cDNA, and analyzed on ABI 3700 automated DNA sequencers (PE Applied Biosystems, California, USA) using the manufacturer's protocols. We sequenced 17,502 cDNA clones from the libraries constructed from each tissue and could successfully read 13,132 EST sequences. FIG. 1 shows the proportion of the ESTs sequenced from each tissue.

EXAMPLE III

Bioinformatics Analysis

The chicken EST trace data were base-called using phrep program (Ewing B. & Green P. (1998) Base-calling of automated sequencer traces using phred. II. Error probabilities. *Genome Research* 8, 186-94) from trace chromatogram data of 3'-end EST sequences. The base-called EST data were vector-clipped, clustered, and assembled by using cross-match program and CAP3 program. (Huang X. & Madan A. (1999) CAP3: A DNA sequence assembly program. *Genome Research* 9, 868-77). Clustering and assembly of these ESTs resulted in total 6,957 unique assembled sequences with 1,699 contigs and 5,258 singletons and average number of ESTs per contig was about 4.7.

Figure 2:
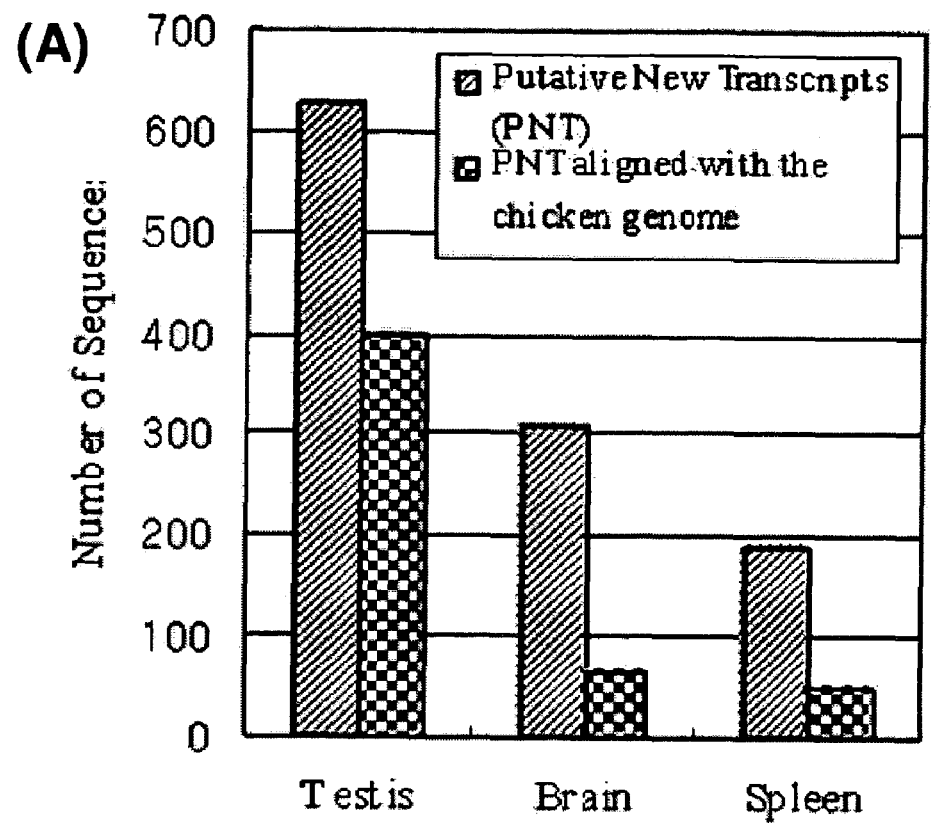
FIG. 2 represents the distribution of putatively new transcript (PNT) and PNT aligned against chicken genome draft sequences of the University of California Santa Cruz (UCSC) genome browser in each tissue. 1,176 putative novel transcripts were retrieved after the comparison and filtering, and mainly consisted of singletons (96%) in contrast with a small portion of contigs (4%). (A) The distribution of PNT singletons and PNT singletons aligned. (B) The distribution of PNT contigs and PNT contigs aligned.
Figure 2:
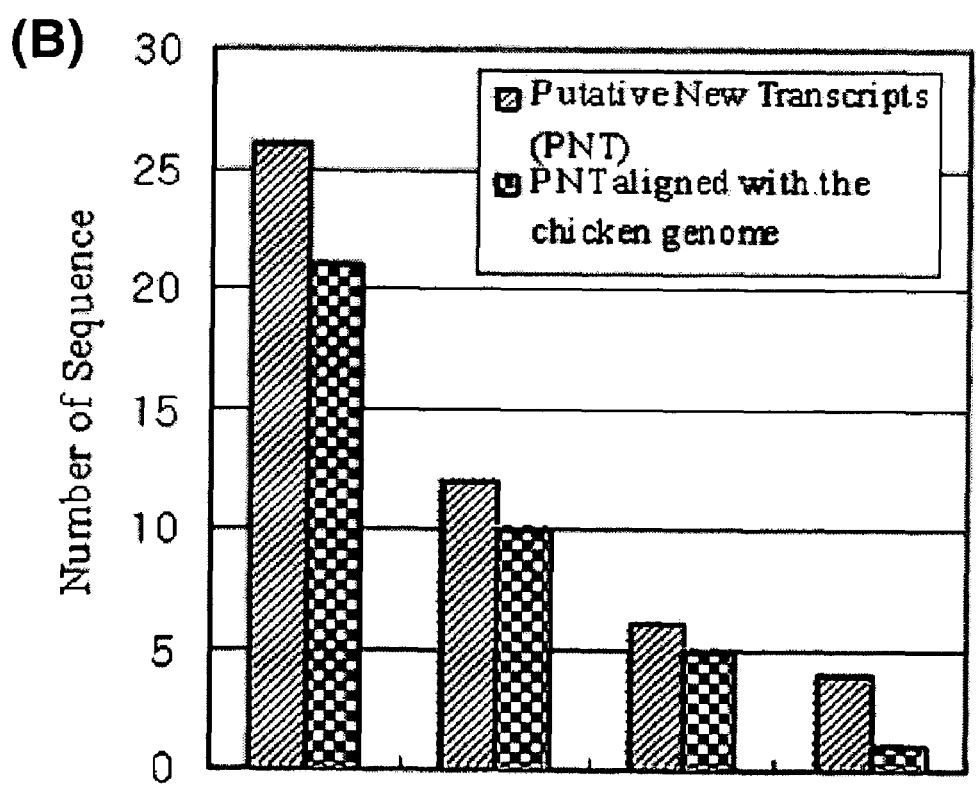

To identify putative novel transcripts, a sequence comparison between GGGI (Release 7.0) and our unique sequences were performed using stand-alone blast program (version 2.2.9) of the NCBI. The sequences with no blast hits were represented as the putative novel transcripts. In case of less than 300 bp in the sequenced length, we threw away for the fidelity of analysis. Total of 1,176 putative novel transcripts have resulted after the comparison and filtering, and mainly consisted of singletons (96%) in contrast with a small portion of contigs (4%). However, most of the sequences (93%) had no significant hits to the non-redundant (nr) protein databases of the NCBI in blastx search (e-value<0.00001). It might result from the low quality of sequences or sequencing errors. To filter out the low quality sequences, therefore, we aligned the EST sequences against chicken genome draft sequences of the University of California Santa Cruz (UCSC) genome browser. We used arbitrarily high degree of stringent condition for the transcript alignment with the genome sequences (score>500). About half of the sequences were screened out and finally resulted in 553 sequences (FIG. 2). As shown in FIG. 2, a large number (76%) of the assembled sequences that were tentatively considered as a novel transcript after aligned with the genome were mainly from testis-originated ESTs.

Furthermore, analysis of exon/intron structure of the contigs among the tentatively- and highly-qualified novel transcripts showed that the large portion of novel transcripts have intronless structure in coding regions. We used the Fisher's exact test to compare two independent binomial proportions between the EST contigs and others; the numbers of intronless contigs versus that of multiple exons contigs. Of the 37 contigs, 30 (81%) contigs have intronless structure in coding regions and this ratio of intronless contigs was too higher than 30% expected under the assumption of random sampling, in which one hundred TC sequences were randomly selected from the GGGI data for the analysis. The two-tailed P value was less than 0.0001 indicating extremely significant.

The large portion of single coding structure might be resulted from relatively short segment of the contigs or other systematic bias. However, many genes have been recently reported to be intronless and expressed exclusively in testicular germ cells (Hickox D. M., et al., (2002) Identification of a novel testis-specific member of the phosphatidylethanolamine binding protein family, pebp-2. *Biology of Reproduction* 67, 917-27; Miyagawa Y., et al., (2002) Molecular cloning and characterization of the human orthologue of male germ cell-specific actin capping protein alpha3 (cpalpha3). *Molecular Human Reproduction* 8, 531-9; Hisano M., et al., (2003) Methylation of CpG dinucleotides in the open reading frame of a testicular germ cell-specific intronless gene, Tact1/Act17b, represses its expression in somatic cells. *Nucleic Acids Research* 31, 4797-804; Truong A., et al., (2003) Isolation and expression analysis of the canine insulin-like factor 3 gene. *Biology of Reproduction* 69, 1658-64; Hao Z., et al., (2004) Expression analysis of the human testis-specific serine/threonine kinase (TSSK) homologues. A TSSK member is present in the equatorial segment of human sperm. *Molecular Human Reproduction* 10, 433-44; Choi I., et al., (2004) Characterization and comparative genomic analysis of intronless Adams with testicular gene expression. *Genomics* 83, 636-46). Some of these genes have functionality and the others may be non-functional pseudo-genes. One proposed mechanism of intron loss is reverse transcription of a proceesed mRNA followed by gene conversion. Betran et al. (Retroposed new genes out of the X in *Drosophila*. *Genome Research*, 12:1854-9 (2002)) suggested that these retrogenes showed a significant excess of retrogenes that originated from the X chromosome in *Drosophila*. Furthermore, most of the X-derived autosomal retrogenes had evolved a testis expression pattern.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for identifying a testicular cell of a chicken, which comprises the steps of:
(a) isolating mRNA from a cell of a chicken,
(b) reverse transcribing the mRNA to obtain cDNA,
(c) hybridizing the cDNA with the nucleotide sequence of SEQ ID NO: 7, and
(d) analyzing the occurrence of the hybridization of step (c), wherein the occurrence of the hybridization is indicative of a testicular cell.

* * * * *

UNITED STATES PATENT AND TRADEMARK OFFICE
CERTIFICATE OF CORRECTION

PATENT NO.        : 7,427,481 B2                                        Page 1 of 1
APPLICATION NO. : 11/212222
DATED             : September 23, 2008
INVENTOR(S)       : Shin et al.

It is certified that error appears in the above-identified patent and that said Letters Patent is hereby corrected as shown below:

On the Title Page Item [73], Under Assignee:, add --Seoul National University Industry Foundation, Seoul (KR)--.

Signed and Sealed this

Seventeenth Day of March, 2009

JOHN DOLL
*Acting Director of the United States Patent and Trademark Office*